United States Patent [19]

Chang

[11] 4,409,386
[45] Oct. 11, 1983

[54] SEPARATION OF 3,4-DICHLOROANILINE
[75] Inventor: Tzu-Ching Chang, Wilmington, Del.
[73] Assignee: E. I. Du Pont de Nemours and Company, Wilmington, Del.
[21] Appl. No.: 405,757
[22] Filed: Aug. 6, 1982
[51] Int. Cl.³ ............................................. C07C 85/26
[52] U.S. Cl. ................................... 564/438; 564/442; 564/497
[58] Field of Search .................. 564/438, 497, 442
[56] References Cited
U.S. PATENT DOCUMENTS

| | | | |
|---|---|---|---|
| 1,942,838 | 1/1934 | Semon | 564/438 X |
| 2,408,975 | 10/1946 | Engel | 564/438 X |
| 3,251,880 | 5/1966 | Gentry | 564/438 X |
| 4,174,351 | 11/1979 | Shoffner | 260/563 |

FOREIGN PATENT DOCUMENTS 34-808425 2/1959 Japan ..................................... 564/438

OTHER PUBLICATIONS

"Dissociation Extraction Part 1: General Theory", Anwar et al., Trans. Instn. Chem. Engrs., vol. 49, (1971).
"Separation of Close Boiling Substituted Phenols by Dissociation Extraction", Wadekar et al., J. Chem. Tech. Biotechnol 31, pp. 279–284 (1981).

*Primary Examiner*—John Doll

[57] ABSTRACT

An acid extraction process for separating 3,4-dichloroaniline from 2,3-dichloroaniline and 2,5-dichloroaniline is disclosed. The process involves selectively forming 3,4-dichloroaniline hydrochloride, since it has a higher basicity than the other dichloroaniline isomers, in a multiple stage extraction unit. An aqueous solution of 3,4-dichloroaniline hydrochloride is removed from the multiple stage extraction unit and neutralized with a base to form an immiscible mixture of an aqueous salt solution and 3,4-dichloroaniline which are separated by decantation.

2 Claims, 1 Drawing Figure

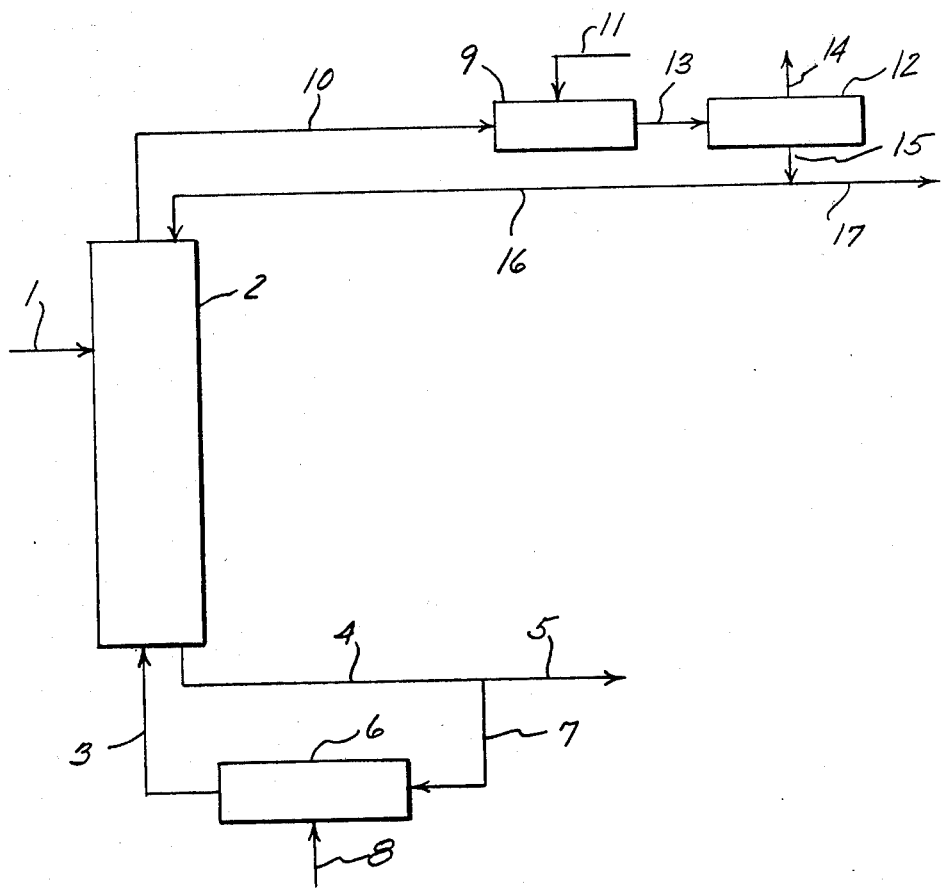

SEPARATION OF 3,4-DICHLOROANILINE

BACKGROUND OF THE INVENTION

The present invention relates to a process for the separation of dichloroaniline isomers by treatment with aqueous hydrochloric acid, followed by phase separation of the remaining dichloroaniline isomers from the aqueous phase containing hydrochloride salt of 3,4-dichloroaniline.

PRIOR ART

Separation of the weak organic bases 3- and 4-picoline by contacting a solution of the two bases in an organic solvent with an aqueous phase containing a stoichiometric deficiency of a strong acid in relationship to the two bases so that the two bases will compete for the available acid is disclosed by "Dissociation Extraction Part I: General Theory," Anwar et al, Trans. Instn. Chem. Engrs., Vol. 49, 1971. The isomer with the higher dissociation constant, that is with stronger base will react preferentially with the strong acid forming a salt in the aqueous phase thus causing an enrichment of the organic phase with respect to the weaker base. The article claims that, by applying this principle to a multi-stage counter-current operation, products of high purity can be obtained.

Some mixtures of substituted phenols, which are difficult to separate by established methods such as distillation or crystallization, have been separated by dissociation extraction as disclosed in "Separation of Close Boiling Substituted Phenols by Dissociation Extraction," Wadekar et al, J. Chem. Tech. Biotechnol 31, pp 279-284 (1981).

In the past amines which are dissimilar in nature by virtue of possessing different substituents, different structures or position isomers have been selectively separated by various techniques. One such technique is to treat the mixture of amines such as a mixture of m-toluidine and p-toluidine with a reactive carbonyl compound and an acid. The m-toluidine will form an imine while the p-toluidine will form an acid salt. The two can then be recovered as separate aqueous and organic phases. Such a technique is disclosed in U.S. Pat. No. 4,174,351.

SUMMARY OF THE INVENTION

The present invention relates to a process of separating a plurality of dichloroanilines. The dichloroanilines have a significant difference in basicity so that the most basic dichloroaniline can be selectively reacted with hydrochloric acid and be extracted with water. The extraction is done in multiple stages. The dichloroaniline hydrochloride in the aqueous phase is converted to dichloroaniline and recovered by decantation.

BRIEF DESCRIPTION OF THE DRAWING

The drawing is a flow sheet of a primary separation unit of the present invention.

DETAILED DESCRIPTION OF THE DRAWING

In the drawing a mixture of dichloroanilines is fed in line 1 to multiple stage extraction unit 2. An aqueous solution of a hydrochloride salt of the less reactive dichloroanilines is fed to multiple stage extraction unit 2 by means of line 3. The less reactive dichloroanilines are removed neat from multiple stage extraction unit 2 in line 4. A portion of the less reactive dichloroanilines are removed from the system in line 5. The remainder of the less reactive dichloroanilines are sent to neutralizer 6 in line 7. Dilute aqueous hydrochloric acid is fed to neutralizer 6 by means of line 8. The 3,4-dichloroaniline hydrochloride is removed from multiple stage extraction unit 2 and fed to basifier 9 by means of line 10. A base is fed to basifier 9 by means of line 11. The resulting mixture of 3,4-dichloroaniline and aqueous chloride salt solution is fed to decanter 12 by means of line 13. Aqueous chloride salt solution is removed from decanter 12 in line 14. 3,4-Dichloroaniline is removed from decanter 12 by means of line 15. Part of the 3,4-dichloroaniline in line 15 is recycled to multiple stage extraction unit 2 by means of line 16 and the remaining 3,4-dichloroaniline is removed from the system as product in line 17.

DETAILED DESCRIPTION 3,4-Dichloroaniline is produced by nitration of o-dichlorobenzene followed by hydrogen reduction to crude 3,4-dichloroaniline. During nitration 1-nitro-2,3-dichlorobenzene and a small amount of 1-nitro-2,5-dichlorobenzene are also produced. Following hydrogen reduction these become 2,3-dichloroaniline and 2,5-dichloroaniline. In the past these isomers have been separated by distillation.

The amount of hydrochloric acid consumed by the process generally will be from 1 to 2 times the stoichiometric amount of 3,4-dichloroaniline recovered depending on the relative amounts of 3,4-dichloroaniline refluxed in line 16 to the multistage extraction unit 2 and the amount of 3,4-dichloroaniline recovered from the system in line 17.

The process is run in the liquid phase. Since 3,4-dichloroaniline melts at 71° C. the process must be run at an elevated temperature. Generally the temperature will be from 75° to 95° C. Below 75° C. the 3,4-dichloroaniline hydrochloride does not dissolve adequately. At temperatures much above 95° C. pressure equipment is required because of the aqueous phase present.

The concentration of hydrochloric acid in the water used should be between 3.6 and 6.5 percent by weight.

EXAMPLE

A stream containing 87% by weight 3,4-dichloroaniline, 11.5% by weight 2,3-dichloroaniline, 0.8% by weight 2,5-dichloroaniline, 0.2% by weight monochloroanilines, and 0.5% by weight o-dichlorobenzene is fed at a rate of 114 parts by weight per hour in line 1 to multiple stage extraction unit 2. Multiple stage extraction unit 2 contains 7 theoretical stages. 2,3-dichloroaniline, 89 weight percent; 2,5-dichloroaniline, 6 weight percent; 3,4-dichloroaniline, 1 weight percent; and 4 weight percent o-dichlorobenzene are removed in line 4 at a rate of 57 parts by weight per hour. Of this stream in line 4, 14 parts by weight per hour are removed from the system in line 5. The remaining 43 parts per hour are sent in line 7 to neutralizer 6. Hydrochloric acid of 5% concentration by weight is fed to neutralizer 6 in line 8 at a rate of 520 parts per hour to neutralize the dichloroanilines. Aqueous solution of dichloroaniline hydrochlorides is recycled back to the multiple stage extraction unit 2 in line 3. Aqueous solution of dichloroaniline hydrochlorides is removed from the multiple stage extraction unit 2 in line 10 and fed to basifier 9. An aqueous 10% by weight solution of sodium hydroxide is fed, to basifier 9, in line 11 at a rate of 300 parts per hour. The basified dichloroanilines and salt solution from basifier 9 is fed to decanter 12 in line 13. The aqueous solution is removed from decanter 12 in line 14. Dichloroanilines are removed from decanter in line 15 at a rate of 138 parts per hour. This stream of dichloroanilines in line 15 contains 99% by weight 3,4-dichloroaniline, 0.8% by weight 2,3-dichloroaniline, 0.2% by weight monochloroanilines, and negligible concentrations of 2,5-dichloroaniline and o-dichlorobenzene. 100 parts per hour of this purified 3,4-dichloroaniline in line 15 is removed from the system as product in line 17, while the remaining is recycled to multiple stage unit 2 in line 16 at a rate of 38 parts per hour.

The number of moles of organics in the organic phase and in the aqueous phase are not constant throughout the multiple extraction unit 2 as can be seen from the flow rates given in the example. The variation of the molar flow rates is due to (1) hydrolysis of dichloroaniline hydrochlorides in the aqueous phase, with the less base 2,3- and 2,5- isomers undergoing hydrolysis to greater extent than the more base 3,4-isomer, and (2) solubility of dichloroanilines in aqueous phase and the dependence of the solubility on the compositions of the two phases.

I claim:

1. A process of purifying crude mixture of 3,4-dichloroaniline containing 2,3-dichloroaniline and 2,5-dichloroaniline as impurities comprising feeding the crude mixture to a multiple stage extraction unit, removing 2,3-dichloroaniline and 2,5-dichloroaniline from the bottom of the multiple stage extraction unit, removing a portion of said 2,3-dichloroaniline and 2,5-dichloroaniline from the system, feeding the remaining 2,3-dichloroaniline and 2,5-dichloroaniline to a neutralizer, feeding from 3.6 to 6.5 percent by weight aqueous hydrochloric acid to the neutralizer to convert, 2,3-dichloroaniline and 2,5-dichloroaniline to their corresponding hydrochlorides, feeding the hydrochlorides to the multiple stage extraction unit, removing an aqueous solution of 3,4-dichloroaniline hydrochloride from the top of the multiple stage extraction unit, reacting the 3,4-dichloroaniline hydrochloride with a base to form an immiscible mixture of an aqueous chloride salt solution and 3,4-dichloroaniline, decanting the mixture to recover 3,4-dichloroaniline, recycling a portion of the 3,4-dichloroaniline to the multiple stage extraction unit.

2. The process of claim 1 wherein the multiple stage extraction unit is maintained at from 75° to 95° C.

* * * * *